(12) United States Patent
Kim et al.

(10) Patent No.: US 9,200,138 B2
(45) Date of Patent: Dec. 1, 2015

(54) METHOD FOR PREPARING ESTER PLASTICIZER AND ESTER PLASTICIZER PREPARED BY THE SAME

(71) Applicant: LG CHEM, LTD., Seoul (KR)

(72) Inventors: Hyun Kyu Kim, Daejeon (KR); Da Won Jung, Daejeon (KR); Mi Yeon Lee, Daejeon (KR); Dong Hyun Ko, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 14/510,816

(22) Filed: Oct. 9, 2014

(65) Prior Publication Data
US 2015/0025186 A1    Jan. 22, 2015

Related U.S. Application Data

(63) Continuation of application No. PCT/KR2013/005919, filed on Jul. 3, 2013.

(30) Foreign Application Priority Data

Jun. 14, 2013  (KR) .................. 10-2013-0068197
Jul. 3, 2013   (KR) .................. 10-2013-0077986

(51) Int. Cl.
*C08K 5/12*   (2006.01)
*C08L 27/06*  (2006.01)
*C07C 69/82*  (2006.01)
*C07C 67/02*  (2006.01)
*C08K 5/00*   (2006.01)

(52) U.S. Cl.
CPC . *C08K 5/12* (2013.01); *C07C 69/82* (2013.01); *C08K 5/0016* (2013.01); *C08L 27/06* (2013.01); *C08K 2201/014* (2013.01)

(58) Field of Classification Search
CPC ............ C08K 5/12; C08L 27/06; C07C 69/82
USPC ....................... 524/297; 560/96, 76
See application file for complete search history.

(56) References Cited

U.S. PATENT DOCUMENTS

| | | | |
|---|---|---|---|
| 7,276,621 B2 | 10/2007 | Cook et al. | |
| 7,361,779 B1 | 4/2008 | Holt et al. | |
| 2006/0111493 A1 | 5/2006 | Choi et al. | |
| 2007/0179229 A1 * | 8/2007 | Grass ........................... | 524/287 |

FOREIGN PATENT DOCUMENTS

| | | |
|---|---|---|
| CN | 1563159 A | 1/2005 |
| KR | 10-0962877 | 6/2010 |
| KR | 10-2013-0035493 A | 4/2013 |
| KR | 10-2013-0042743 | 4/2013 |
| TW | 200421021 A | 10/2004 |
| TW | 200734300 | 9/2007 |

* cited by examiner

*Primary Examiner* — Ling Choi
*Assistant Examiner* — Ronald Grinsted
(74) *Attorney, Agent, or Firm* — Dentons US LLP

(57) ABSTRACT

Disclosed are a method for preparing an ester plasticizer and an ester plasticizer prepared by the method. More specifically, disclosed are a method for preparing an ester plasticizer comprising trans-esterifying 100 parts by weight of dioctyl terephthalate with 0.1 to 89.9 parts by weight of butyl alcohol, and an ester plasticizer prepared by the method.

Advantageously, provided are a novel method for preparing an ester plasticizer and an ester plasticizer with superior physical properties, prepared by the method.

7 Claims, 2 Drawing Sheets

METHOD FOR PREPARING ESTER PLASTICIZER AND ESTER PLASTICIZER PREPARED BY THE SAME

This application is a Continuation Bypass of International Application PCT/KR2013/005919, with an international filing date of Jul. 3, 2013, which claims priority to and the benefit of Korean Patent Application No. 10-2013-0068197, filed Jun. 14, 2013, and Korean Patent Application No. 10-2013-0077986, filed Jul. 3, 2013, the disclosures of which are incorporated herein by reference in their entirety.

TECHNICAL FIELD

The present invention relates to a method for preparing an ester plasticizer and an ester plasticizer prepared by the method. More specifically, the present invention relates to a novel method for preparing an ester plasticizer and an ester plasticizer with improved physical properties prepared by the method.

BACKGROUND ART

An ester plasticizer is generally produced through an esterification reaction of an acid with an alcohol. The esterification reaction is commonly performed in the presence of an acid or metal catalyst.

Di-2-ethylhexyl phthalate is commonly used as an ester plasticizer, but it is harmful to humans since it is an environmental hormone disturbing endocrine systems, and has limitations to improvement in processability and foamability of resins.

Accordingly, there is an urgent need for an ester plasticizer which is eco-friendly and sufficiently improves processability and foamability of resins, and a method for effectively preparing the same.

DISCLOSURE

Technical Problem

Therefore, the present invention has been made in view of the above problems, and it is an object of the present invention to provide a novel method for preparing an ester plasticizer and an ester plasticizer with improved physical properties prepared by the method.

The object of the present invention and other objects will be accomplished by the disclosure given below.

Technical Solution

In accordance with one aspect of the present invention, the above and other objects can be accomplished by the provision of a method for preparing an ester plasticizer comprising trans-esterifying 100 parts by weight of dioctyl terephthalate with 0.1 to 89.9 parts by weight of butyl alcohol.

In accordance with another aspect of the present invention, provided is a method for preparing an ester plasticizer including a) trans-esterifying 100 parts by weight of dioctyl terephthalate with 0.1 to 89.9 parts by weight of butyl alcohol, and b) removing unreacted butyl alcohol and octyl alcohol as a reaction by-product by combination distillation.

In accordance with another aspect of the present invention, provided is an ester plasticizer including 30 to 99% by weight of dioctyl terephthalate (DOTP), 1 to 70% by weight of butyl octyl terephthalate (BOTP), and 0 to 20% by weight of dibutyl terephthalate (DBTP).

In accordance with another aspect of the present invention, provided is a resin composition including the ester plasticizer, and a vinyl resin or a vinyl chloride resin.

Advantageous Effects

As can be seen from the afore-going, the present invention is effective in providing a novel method for preparing an ester plasticizer and an ester plasticizer with superior physical properties prepared by the method.

BEST MODE

Figure 1:
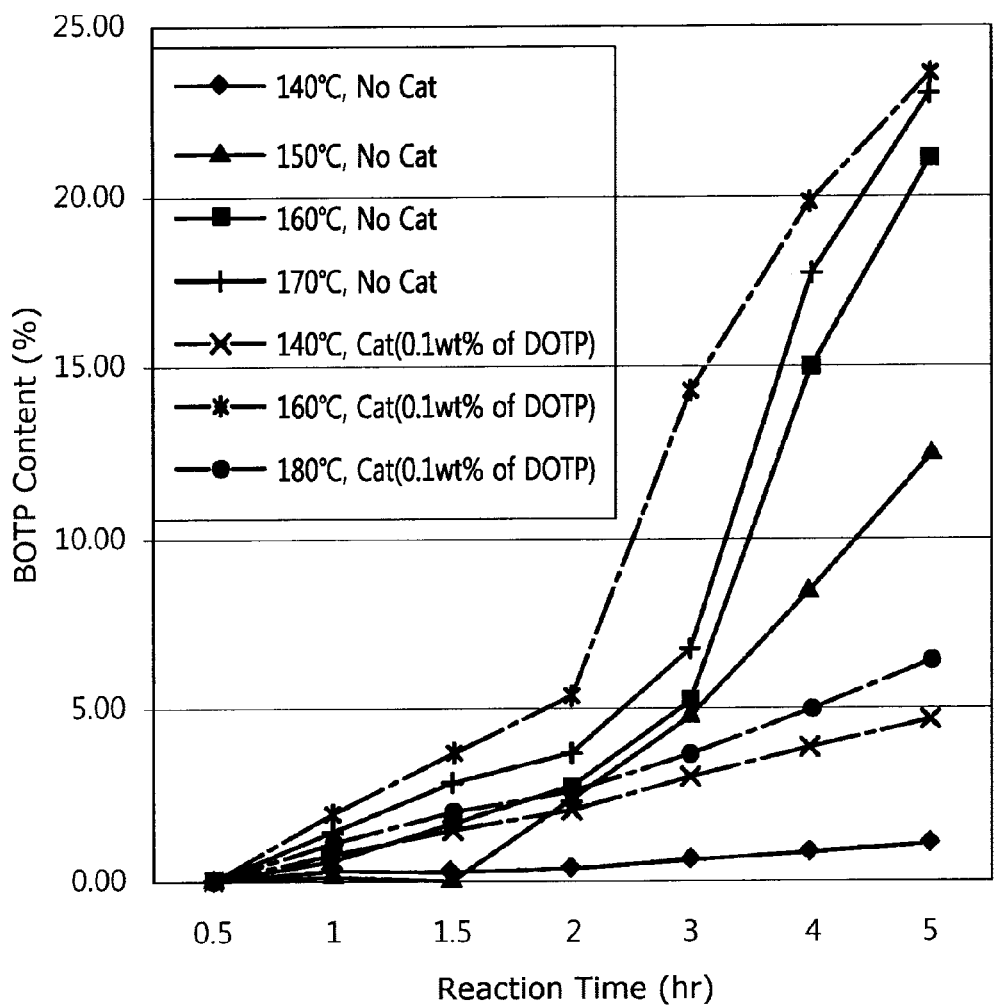
FIG. 1 is a graph showing variation in amount of butyl octyl terephthalate produced according to reaction temperature control and presence of catalyst upon trans-esterification reaction (amount of added butanol: amount corresponding to 10% by weight of dioctyl terephthalate) according to the present invention.

Hereinafter, the present invention will be described in detail.

The method for preparing an ester plasticizer according to the present invention comprises trans-esterifying 100 parts by weight of dioctyl terephthalate with 0.1 to 89.9 parts by weight of butyl alcohol.

The ester plasticizer means an ester compound which is used or can be used as a plasticizer, a composition consisting of such ester compounds, or a composition comprising the ester compound or the ester compounds.

For example, through the trans-esterification reaction, the dioctyl terephthalate is converted into 30 to 99% by weight of the dioctyl terephthalate, 1 to 70% by weight of butyl octyl terephthalate, and 0 to 20% by weight of dibutyl terephthalate. Within this range, there is an effect of obtaining an ester plasticizer which exhibits excellent process efficiency, superior processability and high absorption rate.

In another example, through the trans-esterification reaction, the dioctyl terephthalate is converted into 39 to 80% by weight of the dioctyl terephthalate, 10 to 60% by weight of butyl octyl terephthalate, and 1 to 15% by weight of dibutyl terephthalate. Within this range, there is an effect of obtaining an ester plasticizer which exhibits excellent process efficiency, superior processability and high absorption rate.

In another example, through the trans-esterification reaction, the dioctyl terephthalate is converted into 47 to 70% by weight of the dioctyl terephthalate, 20 to 50% by weight of butyl octyl terephthalate, and 3 to 10% by weight of dibutyl terephthalate. Within this range, there is an effect of obtaining an ester plasticizer which exhibits excellent process efficiency, superior processability and high absorption rate.

In another example, through the trans-esterification reaction, the dioctyl terephthalate is converted into 64.5 to 98.9% by weight of dioctyl terephthalate, 1 to 32% by weight of butyl octyl terephthalate, and 0.1 to 3.5% by weight of dibutyl terephthalate. Within this range, there is an effect of obtaining an ester plasticizer which exhibits excellent process efficiency, superior processability and high absorption rate.

The butyl alcohol may be added in an amount of 0.1 to 89.9 parts by weight, or 3 to 50 parts by weight, based on 100 parts by weight of the dioctyl terephthalate. Within this range, there is an effect of obtaining an ester plasticizer which exhibits excellent process efficiency and much improved processability and foamability.

A molar ratio of the dioctyl terephthalate to the butyl alcohol is for example 1:0.005 to 1:5.0, 1:0.2 to 1:2.5, or 1:0.3 to 1:0.8. Within this range, there is an effect of obtaining an ester plasticizer which exhibits excellent process efficiency and much improved processability and foamability.

The trans-esterification reaction is for example performed at 120° C. to 190° C., 135° C. to 180° C., or 141° C. to 179° C. Within this range, an ester plasticizer with a desired compositional ratio can be obtained within a short time.

A reaction time of the trans-esterification reaction is for example 0.1 to 10 hours, 0.5 to 8 hours or 1 to 6 hours. Within this range, there is an effect of economically obtaining an ester plasticizer with a desired compositional ratio.

The reaction time of the present invention is calculated from a time at which reactants are elevated in temperature and then reach a reaction temperature.

The trans-esterification reaction may be for example performed in the presence of an acid catalyst or a metal catalyst. This is effective in reducing reaction time.

The acid catalyst is for example sulfuric acid, methanesulfonic acid or p-toluenesulfonic acid, and the metal catalyst is for example an organometallic catalyst, a metal oxide catalyst, a metal salt catalyst or a metal.

The metal component is for example tin, titanium, zirconium or the like.

In addition, the trans-esterification reaction is for example a non-catalytic reaction.

For example, the method for preparing an ester plasticizer may further include removing unreacted butyl alcohol and octyl alcohol as a reaction by-product by distillation, after the trans-esterification reaction.

The distillation is for example two-step distillation for independently separating the butanol and the octyl alcohol from each other using a difference in boiling point.

In another example, the distillation may be combination distillation. In this case, there is little compositional change of the plasticizer and there is thus an effect of relatively stably securing a desired ester plasticizer composition.

The combination distillation means that butanol and octyl alcohol are simultaneously distilled.

The ester plasticizer comprises 30 to 99% by weight of dioctyl terephthalate, 1 to 70% by weight of butyl octyl terephthalate, and 0 to 20% by weight of dibutyl terephthalate. Within this range, improvement effects of processability and absorption rate of resins are excellent.

The ester plasticizer for example comprises 39 to 80% by weight of dioctyl terephthalate, 10 to 60% by weight of butyl octyl terephthalate, and 1 to 15% by weight of dibutyl terephthalate. Within this range, processability and absorption rate of resins are excellent.

In another example, the ester plasticizer comprises 47 to 70% by weight of dioctyl terephthalate, 20 to 50% by weight of butyl octyl terephthalate, and 3 to 10% by weight of dibutyl terephthalate. Within this range, processability and absorption rate of resins are excellent.

In another example, the ester plasticizer comprises 64.5 to 98.9% by weight of dioctyl terephthalate, 1 to 32% by weight of butyl octyl terephthalate, and 0.1 to 3.5% by weight of dibutyl terephthalate. Within this range, processability and absorption rate of resins are excellent.

The ester plasticizer is for example an ether-free plasticizer. In this case, there are effects of superior plasticization efficiency and excellent workability.

Ether-free means that an ether component in the plasticizer is present at 1,000 ppm or less, 100 ppm or less, or 10 ppm or less.

The ether component can be for example controlled by starting material, weight ratio between reactants, reaction temperature, reaction time, type of catalyst, amount of catalyst added and the like.

The octyl is for example 2-ethylhexyl. In this case, there are effects of superior processability and absorption rate.

The resin composition according to the present invention comprises the ester plasticizer, and a vinyl resin or vinyl chloride resin.

Any vinyl resin may be used without particular limitation so long as it is accepted in the technical field. In addition, any vinyl chloride resin may be used without particular limitation so long as it is accepted in the technical field.

The ester plasticizer is for example present in an amount of 5 to 100 parts by weight, based on 100 parts by weight of the resin.

The resin composition may for example comprise a filler.

The filler is for example present in an amount of 10 to 300 parts by weight, 50 to 200 parts by weight, or 100 to 200 parts by weight, based on 100 parts by weight of the resin.

The resin composition for example further comprises at least one selected from a stabilizing agent, a pigment, a lubricant and a foaming agent.

The stabilizing agent, pigment, lubricant and foaming agent may for example be present in an amount of 0.1 to 20 parts by weight or 1 to 15 parts by weight, based on 100 parts by weight of the resin.

Now, preferred examples will be given below for a better understanding of the present invention. These examples are provided only to illustrate the present invention and those skilled in the art will appreciate that various alterations and modifications are possible, without departing from the scope and spirit of the invention as disclosed in the accompanying claims.

EXAMPLE

Example 1

1,000 g of dioctyl terephthalate and 70 g of butanol were added to a reactor equipped with a stirrer, a condenser and a decanter, and a trans-esterification reaction was then performed under a nitrogen atmosphere at a reaction temperature of 140° C. without any catalyst for 5 hours to obtain a reaction product comprising 98.9% by weight of dioctyl terephthalate (hereinafter, DOTP), 1.0% by weight of butyl octyl terephthalate (hereinafter, BOTP) and 0.1% by weight of dibutyl terephthalate (hereinafter, DBTP).

The reaction product was subjected to combination distillation to remove the butanol and 2-ethylhexyl alcohol, thereby preparing a final ester plasticizer.

An ether component was detected in an amount lower than 10 ppm from the prepared ester plasticizer.

Variation in amount of produced BOTP (%) according to reaction time during trans-esterification reaction of Example 1 is shown in FIG. 1.

Example 2

A trans-esterification reaction was performed in the same manner as in Example 1, except that the reaction temperature was 160° C. in Example 1, to obtain a reaction product comprising 76.5% by weight of DOTP, 21.5% by weight of BOTP and 2.0% by weight of DBTP. The reaction product was distilled in the same manner as in Example 1 to prepare a final ester plasticizer.

An ether component was detected in an amount lower than 10 ppm from the prepared ester plasticizer.

Variation in amount of produced BOTP (%) according to reaction time during trans-esterification reaction of Example 2 is shown in FIG. 1.

Example 3

A trans-esterification reaction was performed in the same manner as in Example 1, except that an organic acid catalyst was added in an amount (1.0 g) corresponding to 0.1% by weight of an amount of added DOTP in Example 1, to obtain a reaction product comprising 95.0% by weight of DOTP, 4.8% by weight of BOTP and 0.2% by weight of DBTP. The reaction product was distilled in the same manner as in Example 1 to prepare a final ester plasticizer.

An ether component was detected in an amount of 300 ppm from the prepared ester plasticizer.

Variation in amount of produced BOTP (%) according to reaction time during trans-esterification reaction of Example 3 is shown in FIG. 1.

Example 4

A trans-esterification reaction was performed in the same manner as in Example 2, except that an organic acid catalyst was added in an amount (1.0 g) corresponding to 0.1% by weight of an amount of added DOTP in Example 2, to obtain a reaction product comprising 73.6% by weight of DOTP, 24.0% by weight of BOTP and 2.4% by weight of DBTP. The reaction product was distilled in the same manner as in Example 2 to prepare a final ester plasticizer.

An ether component was detected in an amount of 500 ppm from the prepared ester plasticizer.

Variation in amount of produced BOTP (%) according to reaction time during trans-esterification reaction of Example 4 is shown in FIG. 1.

Example 5

A trans-esterification reaction was performed in the same manner as in Example 1, except that the reaction temperature was 180° C. and an organic acid catalyst was added in an amount (1.0 g) corresponding to 0.1% by weight of the amount of added DOTP in Example 1, to obtain a reaction product comprising 93.2% by weight of DOTP, 6.3% by weight of BOTP and 0.5% by weight of DBTP. The reaction product was distilled in the same manner as in Example 1 to prepare a final ester plasticizer.

Variation in amount of produced BOTP (%) according to reaction time during trans-esterification reaction of Example 5 is shown in FIG. 1.

Example 6

1,000 g of DOTP and 130 g of BuOH were added to a reactor equipped with a stirrer, a condenser and a decanter, and a trans-esterification reaction was then performed using an organic acid catalyst in an amount (10.0 g) corresponding to 1.0% by weight of the amount of added DOTP under a nitrogen atmosphere at a reaction temperature of 160° C. for 5 hours to obtain a reaction product comprising 64.5% by weight of DOTP, 32.0% by weight of BOTP and 3.5% by weight of DBTP.

The reaction product was subjected to combination distillation to remove the butanol and the 2-ethylhexyl alcohol, thereby preparing a final ester plasticizer.

Figure 2:
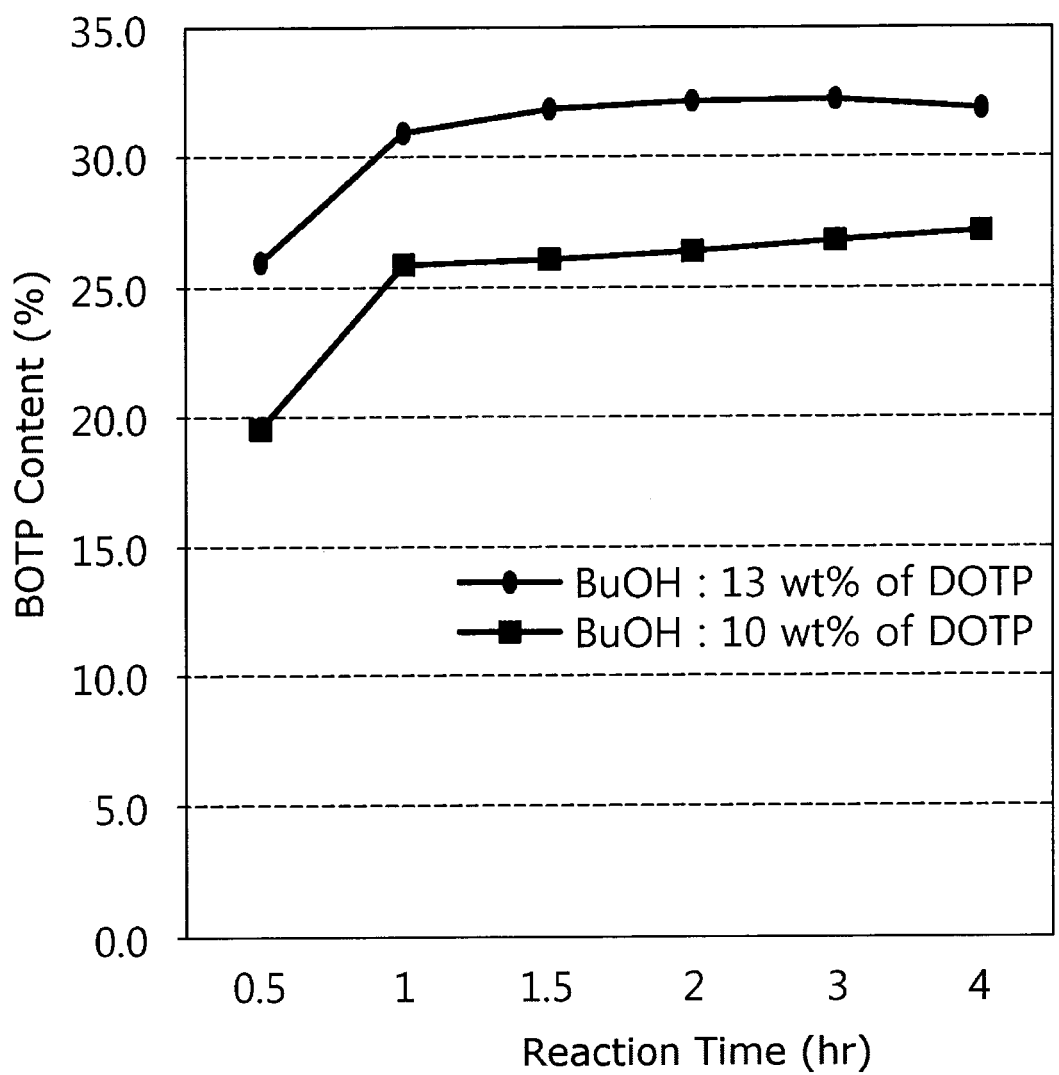
FIG. 2 is a graph showing variation in amount of butyl octyl terephthalate produced according to butanol amount upon the trans-esterification reaction (reaction at 160° C.) according to the present invention.

A variation in amount of produced BOTP (%) according to reaction time during trans-esterification reaction of Example 6 is shown in FIG. 2.

Example 7

A trans-esterification reaction was performed in the same manner as in Example 6, except that BuOH was used in an amount of 100 g in Example 6, to obtain a reaction product comprising 69.9% by weight of DOTP, 27.1% by weight of BOTP and 3.0% by weight of DBTP. The reaction product was distilled in the same manner as in Example 6 to prepare a final ester plasticizer.

Variation in amount of produced BOTP (%) according to reaction time during trans-esterification reaction of Example 7 is shown in FIG. 2.

Example 8

A trans-esterification reaction was performed in the same manner as in Example 7, except that butanol and 2-ethylhexyl alcohol were removed by two-step distillation, instead of the combination distillation, in Example 7, to obtain a final ester plasticizer having a ratio (weight ratio of DOTP, BOTP and DBTP, of 88.1:10.7:1.2.

Example 9

A trans-esterification reaction was performed in the same manner as in Example 1, except that, the reaction temperature was 150° C. in Example 1, to obtain a reaction product comprising 86.5% by weight of DOTP, 12.5% by weight of BOTP and 1.0% by weight of DBTP. The reaction product was distilled in the same manner as in Example 1 to prepare a final ester plasticizer.

An ether component was detected in an amount of 200 ppm from the prepared ester plasticizer.

Variation in amount of produced BOTP (%) according to reaction time during trans-esterification reaction of Example 9 is shown in FIG. 1.

Example 10

A trans-esterification reaction was performed in the same manner as in Example 1, except that the reaction temperature was 170° C. in Example 1, to obtain a reaction product comprising 74.4% by weight of DOTP, 23.1% by weight of BOTP and 2.5% by weight of DBTP. The reaction product was distilled in the same manner as in Example 1 to prepare a final ester plasticizer.

Variation in amount of produced BOTP (%) according to reaction time during trans-esterification reaction of Example 10 is shown in FIG. 1.

Comparative Example 1

A trans-esterification reaction was performed in the same manner as in Example 1, except that, in Example 4, 1,000 g of DBTP was used instead of DOTP, 300 g of 2-ethylhexyl alcohol was added instead of BuOH, and the trans-esterification reaction was performed for 5 hours to obtain a reaction product comprising 4.3% by weight of DOTP, 1.0% by weight of BOTP and 94.7% by weight of DBTP. The reaction product was distilled in the same manner as in Example 1 to prepare a final ester plasticizer.

Comparative Example 2

A trans-esterification reaction was performed in the same manner as in Example 4, except that the butanol was added in an amount (900 g) corresponding to 90% by weight of the DOTP to obtain a reaction product comprising 17.20% by weight of DOTP, 72.0% by weight of BOTP and 10.8% by weight of DBTP. The reaction product was distilled in the same manner as in Example 1 to prepare a final ester plasticizer.

Comparative Example 3

498.3 g of terephthalic acid, 111.0 g of n-butanol and 976.5 g of 2-ethyl hexanol were subjected to esterification reaction using 32 g of 70% methanesulfonic acid as an organic acid catalyst in a five-neck round flask equipped with a temperature sensor, a mechanical stirrer, a condenser, a decanter and a nitrogen injector, for about 5 hours, while slowly elevating temperature from 140° C. to 180° C., and the reaction product was cooled and washed with water once and dealcoholized by heating under reduced pressure to prepare a final ester plasticizer.

The prepared ester plasticizer comprised 19.5% by weight of DOTP, 75.5% by weight of BOTP and 5.0% by weight of DBTP, and the ether component was present at 32,000 ppm.

Test Example

Physical properties of plasticizers prepared in Examples 1 to 10 and Comparative Examples 1 and 2 were measured in accordance with the following method and results thus obtained are shown in the following Table 1 and FIGS. 1 and 2.

Contents (wt %) of DOTP, BOTP and DBTP: measured using a gas chromatograph produced by Agilent Technologies (Agilent 7890 GC, column: HP-5, carrier gas: helium).

Ether content: measured using a gas chromatograph produced by Agilent Technologies (Agilent 7890 GC, column: HP-5, carrier gas: helium).

Absorption rate: evaluated by measuring a time at which a resin is mixed with a plasticizer using a mixer (product name: Brabender) under mixing conditions of 77° C., 60 rpm, PVC (product name: LS 100) 400 g and plasticizer 200 g, and a torque of the mixer is then stabilized.

Foamability: 100 parts by weight of PVC (product name: PB 900), 75 parts by weight of a plasticizer, 130 parts by weight of a filler, 4 parts by weight of a stabilizing agent, 13 parts by weight of $TiO_2$ and 3 parts by weight of a foaming agent were mixed to obtain a sol, the sol was thinly coated on a base paper (paper) used for wallpaper and was then foamed at 230° C. for 70 seconds, the cross-section of the paper was cut, a cell state was measured using an optical microscope, and size, shape and arrangement uniformity of the cell were evaluated on a scale of 1 (good) to 5 (bad).

TABLE 1

| | Catalyst (%) | Reaction temperature (° C.) | Reaction time (h) | Absorption rate (m:s) | Foamability |
|---|---|---|---|---|---|
| Ex. 1 | Not added | 140 | 5 | 6:10 | 3 |
| Ex. 2 | Not added | 160 | 5 | 4:30 | 1 |
| Ex. 3 | 0.1 | 140 | 5 | 6:00 | 4 |
| Ex. 4 | 0.1 | 160 | 5 | 4:11 | 1 |
| Ex. 5 | 0.1 | 180 | 5 | 5:48 | 3 |
| Ex. 6 | 1.0 | 160 | 4 | 3:42 | 1 |
| Ex. 7 | 1.0 | 160 | 4 | 4:01 | 1 |
| Ex. 8 | 1.0 | 160 | 4 | 5:58 | 2 |
| Ex. 9 | Not added | 150 | 5 | 5:50 | 3 |
| Ex. 10 | Not added | 170 | 5 | 4:25 | 1 |
| Comp. Ex. 1 | 0.1 | 160 | 5 | 2:13 | 4 |
| Comp. Ex. 2 | 0.1 | 160 | 5 | 2:52 | 3 |
| Comp. Ex. 3 | 4.5 | 140-180 | 5 | 2:50 | 3 |

Foamability: 1 (Good) to 5 (Bad)

In accordance with the method for preparing ester plasticizers according to the present invention, butyl octyl terephthalate having a desired composition can be freely prepared, and the ester plasticizers prepared therefrom (Examples 1 to 10) have high absorption rates of 3:42 to 6:10 (m:s) and exhibit superior workability and foamability of resins, as can be seen from Table 1 above.

However, it can be seen that ester plasticizers (Comparative Examples 1 and 2) prepared by a method which is different from the method for preparing an ester plasticizer of the present invention aggravates gelation due to considerably high absorption rate and have considerably low workability and foamability.

In addition, it can be seen that the method for preparing an ester plasticizer according to the present invention has a short reaction time and consumes butyl alcohol well soluble in water, and does not yield by-products, thus advantageously causing almost no wastewater disposal problems.

As can be seen from FIG. 1, in the case of Examples 1 to 5 and Examples 9 and 10, the trans-esterification reaction according to the present invention, regardless of using of a catalyst, causes a great increase in amount of produced BOTP at a reaction temperature which is higher than about 140° C. and is lower than about 180° C. and enables easy production of an ester plasticizer having a desired compositional ratio.

In addition, as can be seen from FIG. 2 (Examples 6 and 7), the trans-esterification reaction according to the present invention causes a constant increase in amount of produced BOTP as an amount of butyl alcohol added increases.

In addition, it can be seen that, when residual alcohol is removed by other distillation method after the trans-esterification reaction according to the present invention, two-step distillation (Example 8) exhibits a great decrease in amount of produced BOTP, as compared to combination distillation (Examples 6 and 7).

In addition, it can be seen that, when an ester plasticizer is prepared by esterification reaction (Comparative Example 3), as compared to the trans-esterification reaction according to the present invention, it is relatively difficult to control a preparation process, there are many problems associated with wastewater disposal, and it is not easy to obtain a desired ester plasticizer composition.

The invention claimed is:

1. A method for preparing an ester plasticizer comprising trans-esterifying 100 parts by weight of dioctyl terephthalate with 0.1 to 89.9 parts by weight of butyl alcohol wherein the trans-esterification reaction converts the dioctyl terephthalate into 30 to 99% by weight of the dioctyl terephthalate, 1 to 70% by weight of butyl octyl terephthalate, and 0 to 20% by weight of dibutyl terephthalate.

2. The method according to claim 1, wherein the butyl alcohol is present in an amount of 1 to 50 parts by weight.

3. The method according to claim 1, wherein a molar ratio of the dioctyl terephthalate to the butyl alcohol is 1:0.005 to 1:5.0.

4. The method according to claim 3, wherein the molar ratio of the dioctyl terephthalate to the butyl alcohol is 1:0.2 to 1:2.5.

5. The method according to claim 1, wherein the trans-esterification reaction is performed at 120° C. to 190° C.

6. The method according to claim 1, wherein the trans-esterification reaction is a non-catalytic reaction.

7. A method for preparing an ester plasticizer comprising:
   a) trans-esterifying 100 parts by weight of dioctyl terephthalate with 0.1 to 89.9 parts by weight of butyl alcohol; and
   b) removing unreacted butyl alcohol and octyl alcohol as a reaction by-product by combination distillation.

* * * * *